United States Patent [19]

Conche et al.

[11] Patent Number: 4,516,436

[45] Date of Patent: May 14, 1985

[54] LIQUID SAMPLING BENCH

[75] Inventors: Francois Conche, Les Mureaux; Pierre Naujalis, Orly, both of France

[73] Assignee: Commissariat a l'Energie Atomique, Paris, France

[21] Appl. No.: 435,353

[22] Filed: Oct. 20, 1982

[30] Foreign Application Priority Data

Oct. 26, 1981 [FR] France ............... 81 20039

[51] Int. Cl.³ .............................................. G01N 1/14
[52] U.S. Cl. ............................. 73/863.85; 73/864.31; 73/864.52
[58] Field of Search ........... 73/863.31, 863.81, 864.23, 73/864.31, 864.52

[56] References Cited

U.S. PATENT DOCUMENTS 2,968,183 1/1961 Hannaford ....................... 73/864.31
3,383,923 5/1968 Conche ............................ 73/864.52
4,120,662 10/1978 Fosslien .

FOREIGN PATENT DOCUMENTS 2642065 12/1977 Fed. Rep. of Germany .
1437674 3/1966 France .
1559181 3/1969 France .
1111114 4/1968 United Kingdom ............. 73/863.86

Primary Examiner—S. Clement Swisher
Attorney, Agent, or Firm—Oblon, Fisher, Spivak, McClelland & Maier

[57] ABSTRACT

The present invention relates to a liquid sampling bench of the type in which sampling takes place by means of a container sealed by an elastic plug, which is perforated on a hollow needle connected to a tank containing the liquid to be sampled. The latter is positioned beneath a biological protection slab and comprises a sealed vessel located beneath the slab and integral therewith and which contains the end fittings of the hollow needles. It also comprises a mechanical device for introducing and manipulating the containers and whereof at least the lower part traverses the slab and terminates in the vessel level with the needle end fittings. Application is to sampling radioactive liquids in the nuclear industry.

8 Claims, 7 Drawing Figures

LIQUID SAMPLING BENCH

BACKGROUND OF THE INVENTION

The present invention relates to a liquid sampling bench and particularly to a bench for taking radioactive liquid samples.

The remote taking of active solution samples in chemical units for the processing of irradiated fuels is carried out by means of so-called "sampling benches".

The vessels containing the radioactive liquids to be sampled are located beneath a biological protection slab, whose upper part serves as a working plane. The vessels are located at distances, which can represent several dozen meters. The liquid to be sampled is raised from these vessels to the level of the sampling bench and preferably continuously circulates. The plug, which is made from a flexible and elastic material, of a container called a jug or pot, which is previously placed under vacuum, is pricked at its end by a needle connected to the stream of liquid to be sampled. After filling, the container is transferred from the sampling bench to an analytical laboratory. Such benches are described in French Pat. Nos. 1 401 298, and 1 401 405, as well as in certificate of addition No. 2 058 751 to French Pat. No. 1 401 298. These known benches essentially comprise, within a glove box, a series of liquid intakes by means of hollow needle end fittings connected to the vessels containing the radioactive liquids to be dosed, means for introducing the containers into the glove box and for removing the containers from the glove box, whereby handling means make it possible to displace the containers within the glove box. The handling means are fixed to a tool holder and are in general of three types, namely an unplugging tool for the needle intake end fittings, a container handling tool and a tool for removing and refitting the needles.

In such benches, the ends of the end fittings are arranged in accordance with at least one circumferential arc. Above these end fittings and within the glove box, there is a support which rotates about a first axis. On said support a tool holder can rotate about a second axis differing from the first, whilst said tool holder can also move along the second axis. The tools to be used for taking the samples are positioned on the tool holder, in positions off-centred parallel to the second axis and equidistant therefrom.

French certificate of addition No. 2 058 751 describes a number of improvements whereof one relates to an easily changeable short needle end fitting.

These sampling benches operate correctly, but have a certain number of disadvantages. Firstly the benches of the above type are disposed within a glove box, which is itself positioned above the concrete biological protection slab. To provide protection against alpha particles, the system of panels of the glove box and the tools are mounted with gaskets. Furthermore, in order to provide protection against gamma rays, it is necessary for the upper mechanical part of the tools to be formed from solid members corresponding to a protection of at least 7 cm of lead. Moreover, the periphery of the bench is surrounded by lead plates and the face on the working side is provided with a porthole and tongs for performing manipulations in the glove box. In this case, the glove box and its biological protection means form a cumbersome and very heavy assembly.

Certificate of addition No. 2 058 751 proposes the automatic extraction of the filled container and the transportation thereof out of the vessel bench by means of a pneumatic outlet means. For this purpose a mechanical device for the conditioning and removal of the container is described, which makes it possible to automatically confine the container in a slide and to pneumatically remove the container-slide assembly. These mechanical devices are relatively complex and it is desirable to limit their number in order to increase the reliability of the apparatus system.

Moreover, in the aforementioned benches, the end fittings have a certain slope, instead of being positioned vertically. The tools also have a certain slope with respect to the vertical and operate in accordance with an oblique axis. This arrangement made necessary by the very design of the benches with several end fittings described in the aforementioned patent necessitates a precise positioning and an accurate mechanical construction, whose reliability may be inadequate. Finally, when the container, after filling, is removed from the needle end fitting, a drop is left behind on the outer surface of the flexible, elastic plug, perforated by the needle and said drop can be a dangerous source of contamination.

BRIEF SUMMARY OF THE INVENTION

The present invention relates to a sampling bench, which eliminates these disadvantages through eliminating the glove box and in which the number of mechanical devices is limited.

According to the main feature of the sampling bench according to the invention, which is of the type in which sampling is carried out by means of a container or jug sealed by an elastic plug, which is perforated on a hollow needle connected to a reservoir containing the liquid to be sampled and which is positioned beneath a biological protection slab, it comprises a sealed vessel positioned beneath the protection slab and integral therewith and in which is housed the end fittings of the hollow needles, whilst there is at least one mechanical device for the introduction and manipulation of the containers, whereof at least the lower part traverses the slab and terminates in the vessel above the needle end fittings.

According to a preferred embodiment of the invention, the slab comprises a rotary plug positioned above the aforementioned vessel, the needle end fittings being arranged in accordance with a circular arc or several concentric circular arcs, such that the rotation axis of the plug passes through the centres of these circles. In this case, the mechanical device or devices for the introduction and handling of the containers traverse the rotary plug and are provided with at least one tool holder, positioned at a distance from the plug rotation axis, which is equal to the radius of the circles defined hereinbefore. For ease of handling and to permit their transfer by a pneumatic system, the containers are positioned within receptacles called "slides" and the container-slide assemblies are displaced within the bench.

According to a final feature of the sampling bench according to the invention, each mechanical handling device for the containers comprises at least one vertically positioned helical screw, which is free in rotation and immobilized in translation, which makes it possible to displace a container-slide assembly along a downward shaft, a gripping tool and a drum or cylinder making it possible to displace the container-slide assembly between the downward shaft and the gripping tool.

BRIEF DESCRIPTION OF THE DRAWINGS

Other features and advantages of the invention can be gathered from the following description of non-limitative embodiments, with reference to the attached drawings, wherein show.

DETAILED DESCRIPTION OF THE PREFERRED EMBODIMENTS

Figure 1:
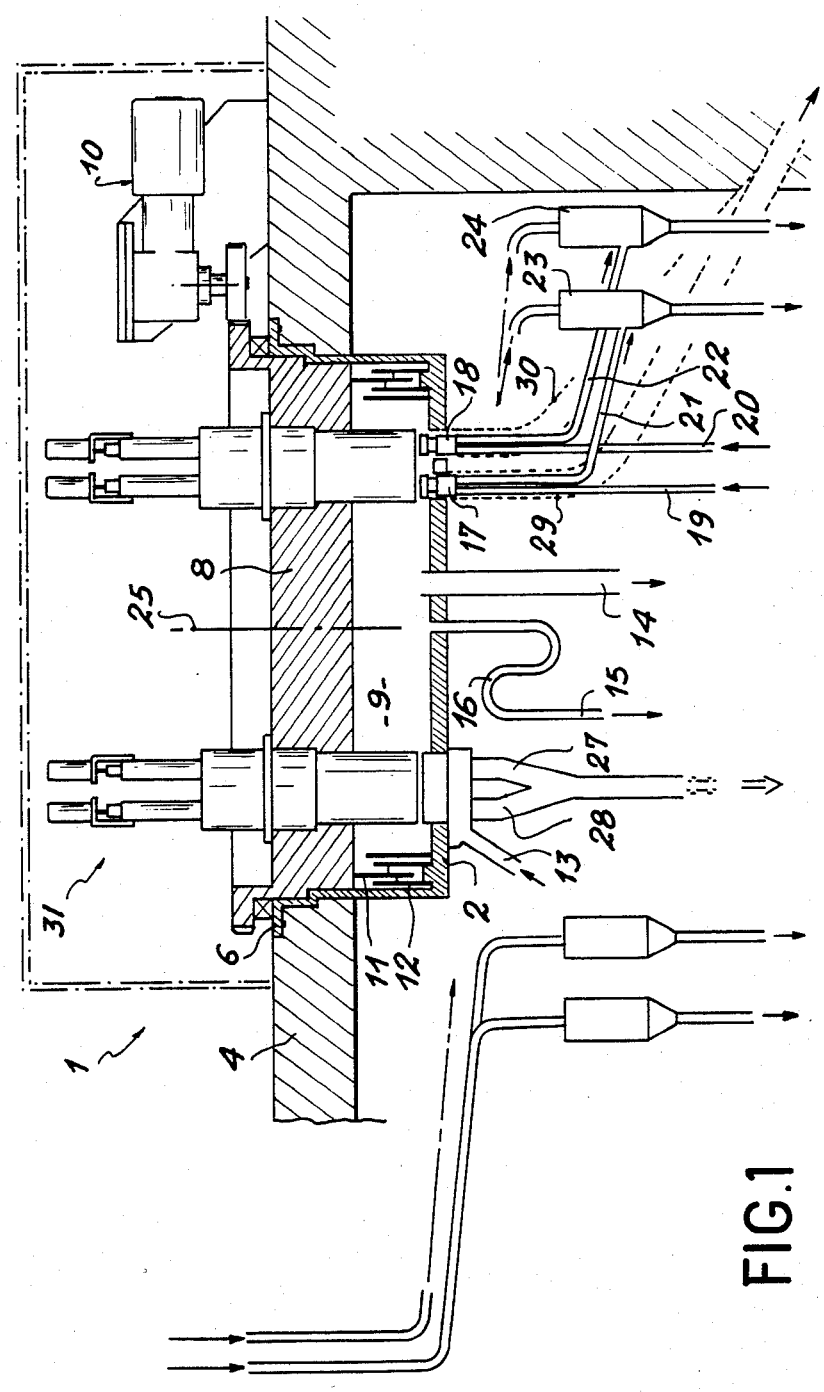
FIG. 1 a diagrammatic, vertical sectional view of a sampling bench according to the invention.

FIG. 1 shows that the sampling bench according to the invention and carrying the general reference 1, firstly comprises a vessel 2, fixed beneath a protective slab 4 and integral therewith so that vessel 2 is in the active area. It is welded to a circular ring 6 supported on the upper part of slab 4. Above vessel 2 is arranged a rotary plug 8, which can be moved by means of an electric motor 10. Thus, a space 9 is defined between plug 8 and vessel 2. In the lower part of plug 8 is fixed a circular sleeve 11, which is immersed in an annular receptacle 12, which is itself fixed to vessel 2 and is located at the periphery of the latter. This device is shown on a larger scale in FIG. 3. It can be seen that receptacle 12 is filled with a liquid, in which is immersed sleeve 11, which forms a hydraulic guard and ensures the necessary sealing. As the interior of vessel 2 is placed under a vacuum, the level of the liquid in receptacle 12 is higher on the inside of sleeve 11 than on the outside. The bottom of the vessel is linked with effluent discharge piping 15, provided with a siphon 16 and connected to piping immersed in a vessel. On the bottom of the vessel, there are two hollow needle end fittings 17, 18, connected by ducts 19, 20 respectively, to a radioactive product storage tank (not shown). The needle end fittings 17, 18 are connected by two discharge ducts 21, 22 to two separators 23, 24 of two devices for circulating the liquid by air lift.

The needle end fittings can be placed on supports, each of which is provided with a supply pipe and a discharge pipe for the liquid to be sampled and separated by an intermediate tank, in order to ensure a good homogenization of the liquid. Advantageously, it is possible to provide a supplementary pipe or drainage duct, which has a significant slope and which connects the lower part of the intermediate tank to the supply pipe, thus permitting an effective draining of the device. It is also possible to provide a cylindrical sleeve open at its lower end and extending the needle end fitting within the intermediate tank. This sleeve serves as a calming means for protecting the needle against turbulence which may occur within the liquid.

End fittings 17 and 18 are located on circular arcs, through whose centre passes the rotation axis 25 of rotary plug 8. The bottom of the vessel also has two outlet orifices for the container-slide assemblies by ducts 27, 28 to the analysis unit. According to a variant, the container-slide assemblies are returned to the analysis unit by introduction devices. In the special case described here, the device has a certain number of end fittings, such as 17, distributed around a first circular arc and a certain number of end fittings, such as 18, distributed around a second circular arc concentric to the first. Ducts 27, 28 issue into the bottom of the vessel at points located on the circles defined by the needle end fittings, namely the circle defined by end fittings such as 17 for duct 27 and the circle defined by end fittings such as 18 for duct 28. The bottom of the vessel also has two waste material discharge orifices, connected to two ducts 29, 30 shown in broken lines on the drawing and positioned on the two aforementioned circles. It is also possible to see two mechanical devices for introducing and manipulating the containers and designated by reference numeral 31. These devices are disposed vertically through plug 8 and lead to the interior of vessel 2.

Figure 2:
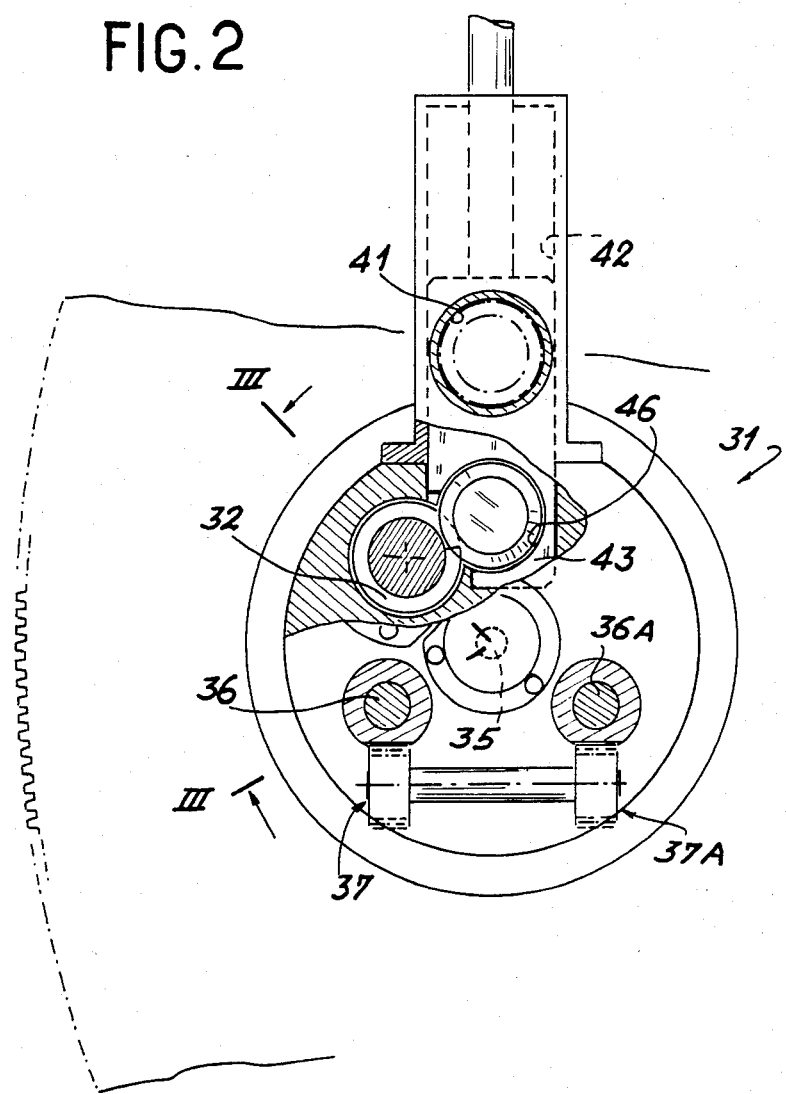
FIG. 2 a plan view of a mechanical device for introducing and manipulating the containers.

The upper part of such a device is shown in the plan view of FIG. 2. A tube 41 enables a container-slide assembly to enter chamber 42, where a piston 43 moves it into contact with a helical screw 32, whose movement enables it to drop to the bottom of a downward shaft 46. A plate, integral with a drum or cylinder, movable about axis 35, makes it possible to bring the container-slide assembly beneath one or other of the tool holders 36, 36a, vertically movable by means of racks 38, 38a cooperating with pinions 37, 37a.

Figure 3:
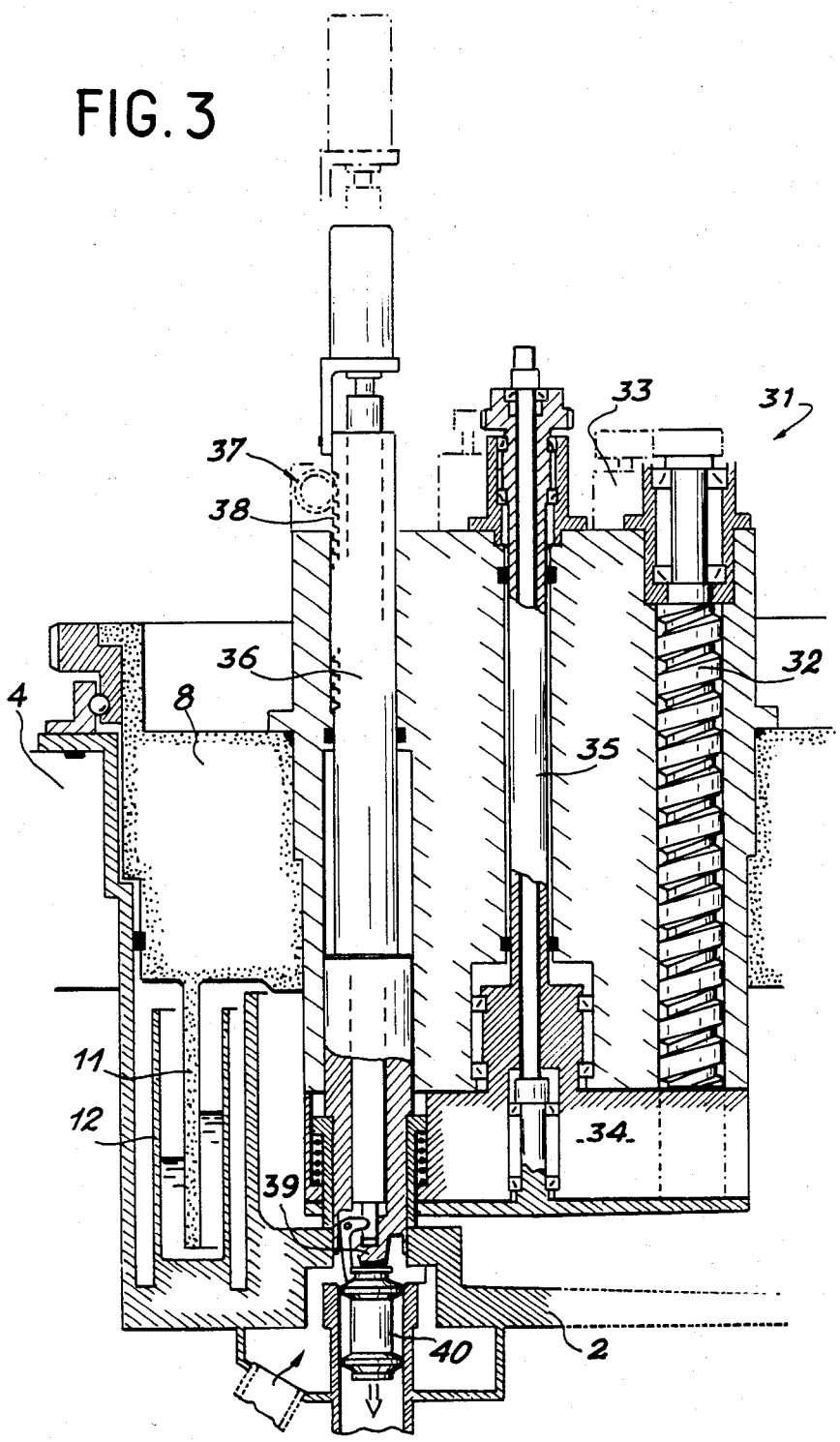
FIG. 3 a larger scale, vertical sectional view along line III—III of FIG. 2.

These devices are shown on the sectional view of FIG. 3. It is possible to see screw 32, which is immobilized in translation but driven in rotation by a motor 33.

Figure 4:
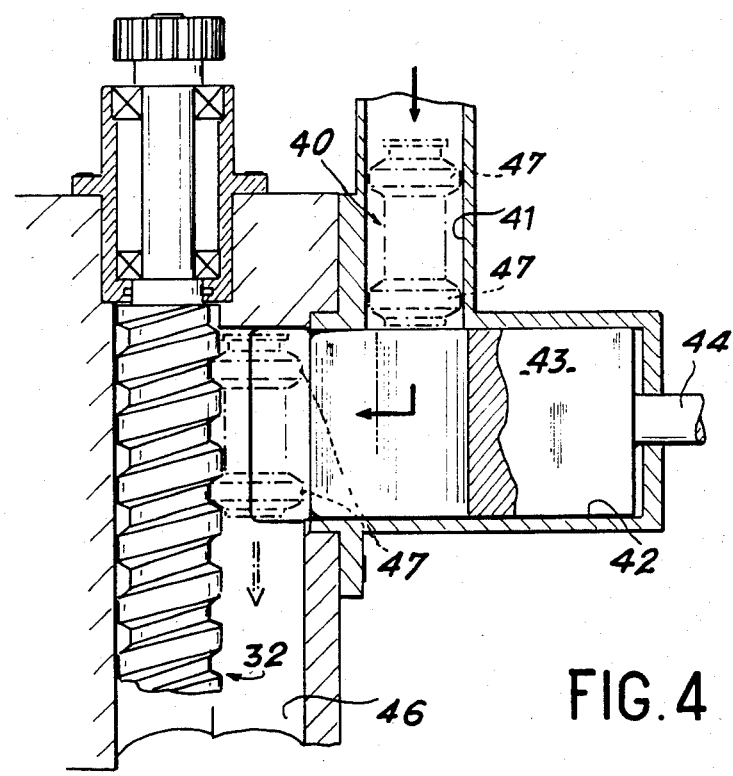
FIG. 4 a diagrammatic sectional view of the upper part of a mechanical handling device for the containers, illustrating the introduction of a container-slide assembly into the device.

The mechanism for introducing containers into the downward shaft will be described hereinafter with reference to FIG. 4. In the lower part of the device there is a drum or cylinder 34, which moves around the axis 35 and makes it possible to bring the container-slide assembly from the lower part of the shaft into a position beneath the tool holder 36 (FIG. 3). The latter is vertically movable by means of the rack 38 cooperating with the pinion 37. The lower part of tool holder 36 is provided with a gripping tool 39 making it possible to grip the container-slide assembly and to bring it above previously selected needle end fitting. The position of the tool holders within the devices such as 31 and the position of the latter in plug 8 are determined in such a way that, by rotating the plug, it is possible to bring a tool holder above any random needle end fitting. In the case where the latter are disposed in accordance with two concentric circular arcs, as is the case in the presently described embodiment, the two tool holders 36, 36a are identical and are positioned at distances from the rotation axis of the plug equal to the radius of the circular arcs defined by the needle end fittings 18, 17 respectively.

Figure 5:
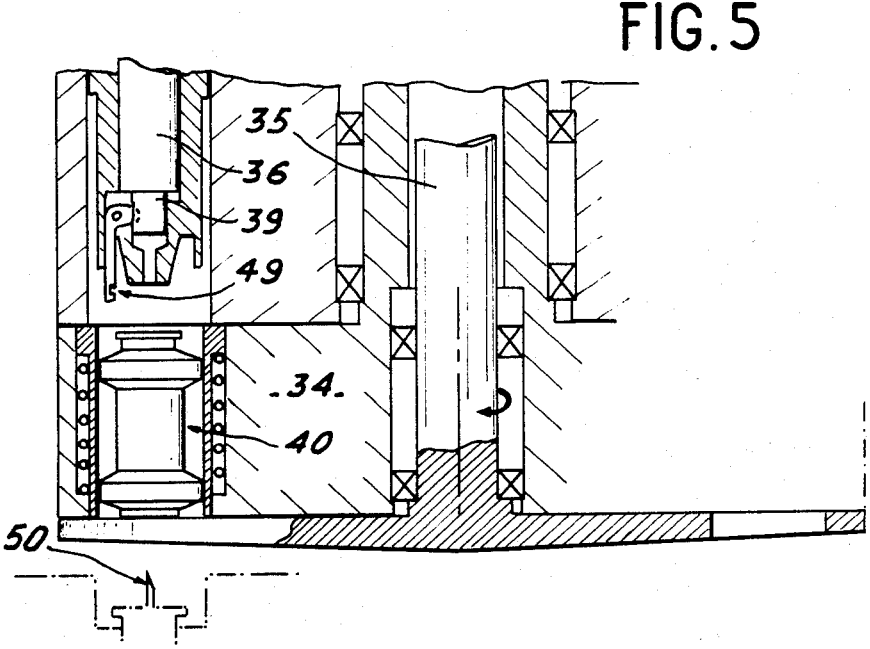
FIG. 5 a diagrammatic sectional view showing such an assembly in the lower part of the mechanical device.

The introduction of a container into device 31 will now be described in detail with reference to FIG. 4. The container-slide assembly 40 is brought by pneumatic transfer into a tube 41 issuing into a chamber 42. A piston 43 controlled by a rod 44 can move within chamber 42. When it is in the retracted position, the assembly 40 drops into chamber 42, then the piston 43 is moved forwards in order to bring the container-slide assembly 40 to the top of the downward shaft 46. However, the assembly does not drop into the shaft, because the two ends of the slide are provided with bulges 47, cooperating with the groove portions of the thread of screw 32. As the latter is immobilized in translation, its rotation ensures the progressive descent of assembly 40 up to drum 34, which is located in the lower part of device 35. (FIG. 5). By rotating the latter about axis 35, the container-slide assembly 40 is brought beneath the tool holder 36. The latter is then lowered until the tongs 49 of tool 39 can grip the container-slide assembly 40 and perforate the latter on needle 50. Once sampling has taken place, the tool holder 36 raises the container-slide assembly and, by an appropriate movement of the rotary plug, the tool holder 36 is brought above a pneumatic starting point for the container-slide assemblies, e.g. above pipe 28 (FIG. 1).

Figure 6:
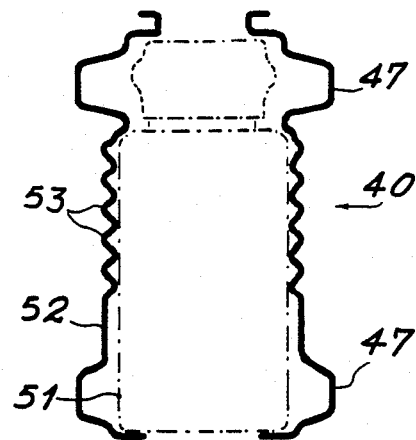
FIG. 6 a diagrammatic view showing a container within a slide.

FIG. 6 shows a container-slide assembly used in the sampling bench according to the invention. This assembly 40 comprises a polyethylene container 51 force-fitted in a cylindrical sleeve 52 or slide, open at its two ends and having on its side wall a certain number of circular bosses 53, which makes it possible to force-fit container 51 in slide 52. Moreover, the latter has at its two ends, bulges 47 cooperating with the thread of helical screw 32, which makes it possible to lower the assembly into shaft 46.

Figure 7:
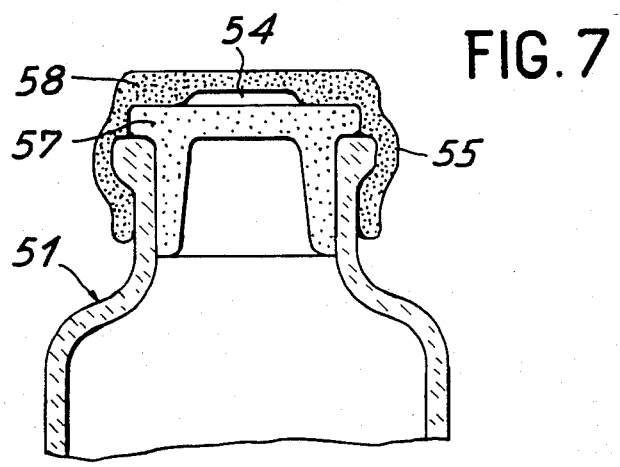
FIG. 7 a diagrammatic sectional view showing a special embodiment of an elastic plug for a sampling container.

FIG. 7 illustrates a special embodiment of the elastic plug 55 of container 51. After sampling, on removing the plug from the needle, there is generally a drop left behind outside the plug and the latter can constitute a dangerous contamination source. To prevent such a risk, plug 55 of slide 51 has an entirely sealed cavity 54, in which the drop is held, when the container is removed from the needle. For example plug 55 can be made in two parts 57, 58, which are stuck together, and whereof only part 58 has a cavity 54.

The sampling bench according to the invention has numerous advantages, the main one being its simplicity. Thus, through the needle end fittings being located in a vessel placed beneath the protective slab, there is no need for glove boxes. Moreover, the mechanical handling devices for the containers have their control members located outside vessel 2, which facilitates positioning checks. They are also simpler than in the prior art sampling benches, because the same tool can be used both for handling the containers and for removing the protective plugs from the needle end fittings and for replacing the latter.

It is obvious that the invention is not limited to the single embodiment described and numerous variants are possible thereto without passing beyond the scope of the invention.

What is claimed is:

1. A bench for sampling liquids by means of a container or jug sealed by an elastic plug, which is perforated on a hollow needle connected to a tank containing the liquid to be sampled, the latter being positioned beneath a biological protection slab, wherein said bench comprises a sealed vessel located beneath the protection slab and integral therewith, in which are located the end fittings of the hollow needles, and at least one mechanical device for introducing and manipulating the containers, whereof at least the lower part traverses the slab and terminates in the vessel level with the needle end fittings, the needle end fittings being disposed on two concentric circular arcs, the slab having a rotary plug, whose rotation axis passes through the center of the circular arcs defined by the needle end fittings, the lower part of said at least one mechanical device for introducing and manipulating the containers traversing the rotary plug, said at least one mechanical device comprising at least one tool holder located at a distance from the rotation axis of the plug equal to the radius of one of the circular arcs defined by the hollow needle end fittings, said at least one mechanical device further comprising rotation means for bringing the containers above a needle located on either of the two circular arcs.

2. A bench for sampling liquids by means of containers sealed by elastic plugs which are perforated by hollow needles each of which is connected to a tank containing a liquid to be sampled, the tanks being positioned beneath a biological protection slab, said bench comprising:
   (a) a sealed vessel located beneath the protection slab and integral therewith, said sealed vessel having a lower surface and upwardly extending sides which are attached to the biological protection slab;
   (b) a plurality of end fittings for hollow needles disposed in the lower surface of said sealed vessel in a circular arc or a plurality of concentric circular arcs;
   (c) a plug disposed in said sealed vessel above the lower surface thereof, said plug being in sealing engagement with said sealed vessel and being rotatable about an axis which passes through the center of the circular arc or arcs on which said end fittings are disposed;
   (d) at least one mechanical device for introducing and manipulating the containers, said at least one mechanical device extending through said rotary plug and terminating in said sealed vessel above the circular arc or arcs on which said end fittings are disposed;
   (e) an upwardly open annular container disposed on the lower surface of said sealed vessel radially outwardly of the circular arc or arcs on which said end fittings are disposed; and
   (f) an annular sleeve which extends downwardly from said rotary plug and which is received in said upwardly open annular container, whereby, when said upwardly open annular container is filled with a liquid to a level above the lower edge of said annular sleeve, said upwardly open annular container and said annular sleeve function as a seal for the volume defined by said vessel and said rotary plug.

3. A bench for sampling liquids by means of containers sealed by elastic plugs which are perforated by hollow needles each of which is connected to a tank containing a liquid to be sampled, the tanks being positioned beneath a biological protection slab, said bench comprising:
   (a) a sealed vessel located beneath the protection slab and integral therewith, said sealed vessel having a lower surface and upwardly extending sides which are attached to the biological protection slab;
   (b) a plurality of end fittings for hollow needles disposed in the lower surface of said sealed vessel in a circular arc or a plurality of concentric circular arcs;
   (c) a plurality of slides within which the containers may be located, said slides permitting the pneumatic transfer of the containers; and
   (d) at least one mechanical device for introducing and manipulating the slides, said at least one mechanical device terminating in said sealed vessel above the circular arc or arcs on which said end fittings are disposed, said at least one mechanical device comprising:
(i) a downwardly directed shaft;
(ii) at least one helical screw which is free in rotation and immobilized in translation, said at least one helical screw operatively engaging said slides to move them in said downwardly directed shaft;
(iii) a gripping tool mounted at the lower end of said at least one mechanical device; and
(iv) means for displacing said slide between said downwardly directed shaft and said gripping tool.

4. A sampling bench according to claim 1, wherein the vessel has on its periphery an annular container, in which is immersed a sleeve integral with the rotary plug.

5. A sampling bench according to claim 1, wherein the container is located within a slide, permitting the pneumatic transfer from the assembly.

6. A sampling bench according to claim 1, wherein the elastic plug of the container has an entirely sealed cavity, traversed by the needle during sampling.

7. A sampling bench according to claims 5 or 6, wherein each mechanical device comprises at least one helical screw, which is free in rotation and immobilized in translation, permitting the movement of the container-slide assembly in a downward shaft, a gripping tool and a drum or cylinder located in the lower part thereof permitting the displacement of the container-slide assembly between the downward shaft and the gripping tool.

8. A sampling bench according to claim 1, wherein each needle end fitting rests on a support, provided with a supply pipe and a discharge pipe for the liquid to be sampled, as well as an intermediate tank located between the supply and discharge pipes, the lower part of said intermediate tank being connected to the supply pipe by a highly sloping drainage duct and the lower part of each end fitting is shaped like a sleeve immersed in the intermediate tank and open at its lower end.

* * * * *